US012582640B2

(12) United States Patent
Polymeropoulos et al.

(10) Patent No.: US 12,582,640 B2
(45) **Date of Patent: *Mar. 24, 2026**

(54) TREATMENT OF LOWER RESPIRATORY TRACT INFECTION WITH TRADIPITANT

(71) Applicant: Vanda Pharmaceuticals Inc., Washington, DC (US)

(72) Inventors: Mihael H. Polymeropoulos, Potomac, MD (US); Christos Polymeropoulos, Potomac, MD (US); Vasilios Polymeropoulos, Potomac, MD (US); Changfu Xiao, Vienna, VA (US)

(73) Assignee: Vanda Pharmaceuticals Inc., Washington, DC (US)

( * ) Notice: Subject to any disclaimer, the term of this patent is extended or adjusted under 35 U.S.C. 154(b) by 748 days.

This patent is subject to a terminal disclaimer.

(21) Appl. No.: 17/906,861

(22) PCT Filed: Mar. 24, 2021

(86) PCT No.: PCT/US2021/023875

§ 371 (c)(1),
(2) Date: Sep. 20, 2022

(87) PCT Pub. No.: WO2021/195205

PCT Pub. Date: Sep. 30, 2021

(65) Prior Publication Data

US 2023/0145932 A1 May 11, 2023

Related U.S. Application Data

(60) Provisional application No. 63/067,298, filed on Aug. 18, 2020, provisional application No. 63/002,323, filed on Mar. 30, 2020, provisional application No. 63/001,248, filed on Mar. 27, 2020, provisional application No. 63/000,477, filed on Mar. 26, 2020.

(51) Int. Cl.

*A61K 31/454* (2006.01)
*A61K 9/00* (2006.01)
*A61P 31/14* (2006.01)

(52) U.S. Cl.

CPC .......... *A61K 31/454* (2013.01); *A61K 9/0019* (2013.01); *A61K 9/0053* (2013.01); *A61P 31/14* (2018.01)

(58) Field of Classification Search

CPC ............................ A61K 31/444; A61K 31/454
See application file for complete search history.

(56) References Cited

U.S. PATENT DOCUMENTS

| | | | |
|---|---|---|---|
| 5,585,385 | A | 12/1996 | Natsugari et al. |
| 6,329,394 | B1 | 12/2001 | Hagan et al. |
| 7,179,804 | B2 | 2/2007 | Amegadzie et al. |
| 7,320,994 | B2 | 1/2008 | Amegadzie et al. |
| 7,381,826 | B2 | 6/2008 | Borghese et al. |
| 7,799,782 | B2 | 9/2010 | Munson et al. |
| 8,772,496 | B2 | 7/2014 | Chen |
| 10,463,655 | B2 | 11/2019 | Polymeropoulos et al. |
| 10,821,099 | B2 | 11/2020 | Polymeropoulos |
| 11,324,735 | B2 * | 5/2022 | Polymeropoulos .. A61K 31/444 |
| 2014/0378521 | A1 | 12/2014 | Zhang et al. |

FOREIGN PATENT DOCUMENTS

| | | | |
|---|---|---|---|
| JP | 2005534627 | A | 11/2005 |
| WO | 2007096782 | A2 | 8/2007 |
| WO | 2018136554 | A1 | 7/2018 |
| WO | 2019099883 | A1 | 5/2019 |

OTHER PUBLICATIONS

Clinical Trails, 2020, pp. 1-6.*
Anonymous, "History of Changes for Study: NCT01919944: Study of Itech Control by VLY-686 in Healthy Volunteers After Intradermal Injections of Substance P," U.S. National Library of Medicine, ClinicalTrials.gov archive, retrieved from: https://clinicaltrials.gov/ct2/history/NCT01919944?A=5&B=5&C=merged on Dec. 16, 2019, 9 pages.
Anonymous, "History of Changes for Study: NCT02004041: Proof of Concept of VLY-686 in Subjects With Treatment-Resistant Pruritus Associated with Atopic Dermatitis," U.S. National Library of Medicine, ClinicalTrials.gov archive, retrieved from: https://clinicaltrials.gov/ct2/history/NCT02004041?A=4&B=4&C=merged on Dec. 16, 2019, 9 pages.
FDA; "Guidence for Industry Exposure-Response Relationships—Study Design, Data Analysis, and Regulatory Applications;" Published Apr. 2003; pp. 1-28.
Bhatia et al., "Role of Inflammatory Mediators in the Pathophysiology of Acute Respiratory Distress Syndrome," The Journal of Pathology, vol. 202, 2004, pp. 145-156, XP055036718.
George et al., "Neurokinin 1 Receptor in Antagonism as a Possible Therapy for Alcoholism," Science Magazine, vol. 319, No. 2869, Mar. 14, 2008, 6 pages.
George et al., "Supporting Online Material for Neurokinin 1 Receptor Antagonism as a Possible Therapy for Alcoholism," Science, vol. 319, No. 2869, Mar. 14, 2008, 14 pages.
International Search Report and Written Opinion for corresponding PCT Application No. PCT/US2021/023875, Jun. 30, 2021, 12 pages.
Sadick Research Group; "Tradipitant in Treatment-Resistant Pruritus Associated With Atopic Dermatitis;" ClinicalTrials.gov Identifier NCT02672410; last Updated Feb. 2, 2016; accessed on Feb. 11, 2016; pp. 3; <https://clinicaltrials.gov/ct2/show/study/NCT02672410?TERM=TRADIPITANT&RANK=3>.
Santini et al., "Aprepitant for Management of Severe Pruritus Related to Biological Cancer Treatments: A Pilot Study," The Lancet, vol. 13; Oct. 2012; Published online Sep. 18, 2012, pp. 1020-1024.

(Continued)

*Primary Examiner* — Rei Tsang Shiao
(74) *Attorney, Agent, or Firm* — Hoffman Warnick LLC

(57) ABSTRACT

Disclosed herein is a method of treatment of a lower respiratory tract infection caused by, e.g., coronavirus disease (COVID-19), influenza, or other virus, comprising treatment with the NK-1 receptor antagonist, tradipitant.

20 Claims, 2 Drawing Sheets

(56) References Cited

OTHER PUBLICATIONS

Stander et al., "Targeting the Neurokinin Receptor 1 with Aprepitant: A Novel Antipruritic Strategy," PLoS One, vol. 6, No. 6, Jan. 1, 2010, 6 pages.
Sun et al., "Particle Size Specifications for Solid Oral Dosage Forms: A Regulatory Perspective," American Pharmaceutical Review, Published May 1, 2010, 9 pages.
Tauscher et al., "Development of the 2nd Generation Neurokinin-1 Receptor Antagonist LY686017 for Social Anxiety Disorder," European Neuropsychophamarcologgy, 2010, Elsevier Science Publishers BV, Amsterdam, NL, vol. 20, No. 2, Feb. 1, 2010, 8 pages.
Trower et al., "Neurokinin-1 Receptor Antagonist Orvepitant is an Effective Inhibitor of Itch-Associated Response in a Mongolian Gerbil Model of Scratching Behaviour," Experimental Dermatology 2014, vol. 23, pp. 853-864.
Wong et al., "Substance P and Neutral Endopeptidase in Development of Acute Respiratory Distress Syndrome Following Fire Smoke Inhalation," American Journal of Physiology—Lung Cellular and Molecular Physiology, American Physiological Society, US, vol. 287, No. 4, Oct. 1, 2004, pp. L859-L866, XP002468167.
Mehboob R, et al., "Aprepitant as a combinant with Dexamethasone reduces the inflammation via Neurokinin 1 Receptor Antagonism in severe to critical Covid-19 patients and potentiates respiratory recovery: A novel therapeutic approach," medRxiv, retrieved from https://www.medrxiv.org/content/10.110 12020.08.01.20166678v3 on Nov. 19, 2021 (Sep. 5, 2020; version posted Dec. 17, 2020).
Anonymous, "Odyssey: A Study to Investigate the Efficacy of Tradipitant in Treating Severe or Critical COVID-19 Infection—Full Text View—ClinicalTrials.gov," ClinicalTrials.gov Identifier NCT04326426, (retrieved from https://clinicaltrials.gov/ct2/show/NC T04326426 on Nov. 19, 2021; last updated Apr. 20, 2020).
Thakur S, et al., "Exploring the magic bullets to identify Achilles' heel in SARS-CoV-2: Delving deeper into the sea of possible therapeutic options in Covid-19 disease: An update," Food and Chemical Toxicology 147 (2021) 11187, pp. 1-22 (available online Nov. 27, 2020).
Mehboob R and Lavezzi AM, "Neuropathological explanations of minimal COVID-19 infection rate in newborns, infants and children—a mystery so far. New insight into the role of Substance P," Journal of the Neurological Sciences 420:117276 (2021; published online Dec. 17, 2020), pp. 1-3.
Aguirre-Siancas EE et al., "Substance P, proinflammatory cytokines, transient receptor potential vanilloid subtype 1 and COVID 19: a working hypothesis," Neurologia (English Edition), 36(2): 184-185 (Mar. 2021).
Smieszek S, "Late Breaking Abstract—Increased Substance P levels in COVID-19 hospitalized patients," European Respiratory Journal 2021; 58: Suppl 65, OA4114 (Nov. 25, 2021).
Hagiwara, D. "Discovery of Low-Molecular Weight Antagonists of Substance P: Recent Developments and Prospects as a Therapeutic Agent," Journal of Synthetic Organic Chemistry (Japan), vol. 52, Issue 5, 1994, pp. 445-452.
Shinya Usui, Decision of Refusal, Japanese Patent Application No. 2021-012356 "Method of Treatment with Tradipitant", pp. 1-3 (Sep. 20, 2022).
Miller, G. "Tackling Alcoholism With Drugs." Science, Apr. 11, 2008, vol. 320, No. 5873, pp. 168-170.
Sinha, R. et al. "Translational and reverse translational research on the role of stress in drugs craving and relapse." Psychopharmacology, Apr. 15, 2011, vol. 218, No. 1, pp. 69-82.
D.B. Jacoby et al., Effects of neurokinin receptor antagonists in virus-infected airways, Am J Physiol Lung Cell and Mol Physiol, 279:L59-L65 (2000).
Takashi Fujii, Discovery and pharmacological properties of selective neurokini-receptor antagonists, FK224 and FK888, Folio Pharmacol Jpn., 106, 193-204 (English abstract at 203) (1995).
J. Smith et al., The Neurokinin-1 Receptor Antagonist Orvepitant Is a Noval Antitussive Therapy for Chronic Refractory Cough, Results From a Phase 2 Pilot Study (Volcano-1), Chest 157(1):111-118 (Jan. 2020).
Notice of Reasons for Rejection for JP Application No. 2021-12356, Mailing No. 083985, mailed Sep. 17, 2024.
Yamamoto, Nobuharu et al., Effect of a novel NK1 receptor antagonist, fosaprepitant (Proemend®), used in patients with oral cancer treated with cisplatin, Oral Tumors 25(3): 109-114 (2013).
Folia Pharmacol. Jpn. (Nippon Yakurigaku Zasshi) 114, Suppl 1, 209P-214P (1999).
Director of New Drugs Division, Pharmaceutical Affairs Bureau, Ministry of Health and Welfare, General Guidelines for Clinical Evaluation of New Drugs, No. 43, addressed to the Chiefs of Health Administration Departments in each prefecture (Jun. 29, 1992).

* cited by examiner

Plot of Time to 2 or more point improvement at day 28
Intent-to-treat Population

TREATMENT OF LOWER RESPIRATORY TRACT INFECTION WITH TRADIPITANT

CROSS REFERENCE TO RELATED APPLICATIONS

The present application is a US national stage entry under 35 U.S.C. § 371 of International Patent Application No. PCT/US2021/023875, filed 24 Mar. 2021, which claims the benefit of U.S. Provisional Application No. 63/000,477, filed 26 Mar. 2020; U.S. Provisional Application No. 63/001,248, filed 27 Mar. 2020; U.S. Provisional Application No. 63/002,323; filed 30 Mar. 2020; and U.S. Provisional Application No. 63/067,298, filed 18 Aug. 2020.

BACKGROUND OF THE INVENTION

The invention relates to a method for the treatment of a lower respiratory tract infection, including associated symptoms, with tradipitant. More particularly, the present invention relates to a method for the treatment of patients suffering from viral pneumonia caused by e.g., COVID-19, influenza, or another respiratory virus. Such treatment provides such patients with the opportunity for accelerated improvement of clinical outcomes associated with severe or critical COVID-19 infection.

Severe acute respiratory syndrome coronavirus 2 (SARS-CoV2) is a novel coronavirus that causes coronavirus disease (COVID-19 disease), which is a highly infectious respiratory illness. COVID-19 was declared a pandemic by the World Health Organization on Mar. 11, 2020, and carries a mortality rate that may exceed 1%. Human to human transmission of the virus is understood to occur via droplets or contact. Common symptoms include fever, chills, cough, shortness of breath or difficulty breathing, fatigue, muscle or body aches, headache, new loss of taste or smell, sore throat, nasal congestion, nausea or vomiting, and diarrhea. The presentation of symptoms including headache, nausea, and vomiting in some patients has caused concern about the neuroinvasive potential of COVID-19.

Additionally, a number of hospitalized patients experience severe pneumonias, with acute respiratory distress syndrome leading to respiratory failure. Cytokine storms have been observed as a complication of COVID-19, and pulmonary fibrosis has also been observed after recovery from COVID-19. The disease pattern is similar to that observed in disease caused by SARS coronavirus (SARS-CoV). An acute need exists for COVID-19 therapies that offer patients improved outcomes, including the potential for reducing morbidity and mortality. Therapeutic success in treating COVID-19 has been claimed through use of the anti-malarial medications chloroquine and hydroxychloroquine, and remdesivir. However, therapies are needed that can prevent or treat the cytokine storm and acute respiratory distress syndrome leading to respiratory failure and high mortality in affected patients with COVID-19, and reduce the inflammatory lung injury and fibrosis that may remain after recovery from COVID-19 infection.

The mammalian tachykinins (neurokinin [NK]) are a family of peptide neurotransmitters that share a common C-terminal sequence. This group includes substance P (SP), neurokinin-A (NKA), and neurokinin-B (NKB). SP, the most abundant NK, preferentially binds to the neurokinin type-1 (NK-1) receptor and is involved in the regulation of many physiological processes, including the neurogenic inflammation of the lung.

NK-1 receptors have been mapped in the central nervous system and were found to have a broad distribution in the brain, including the mid-brain, basal ganglia, hypothalamus, and limbic system. Neurokinin receptors are also widely distributed in the gut, the bronchial tree, and the vascular system.

Tradipitant is a highly potent, selective, centrally penetrating, and orally active NK-1 receptor antagonist, with structure shown below as Formula I:

(I)

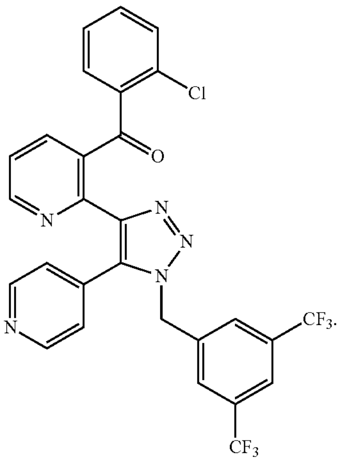

Tradipitant is disclosed in U.S. Pat. No. 7,320,994, and contains six main structural components: the 3,5-bis-trifluoromethylphenyl moiety, two pyridine rings, the triazol ring, the chlorophenyl ring, and the methanone. Tradipitant is known by the chemical names, 2-[1-[[3,5-bis(trifluoromethyl)phenyl]methyl]-5-(4-pyridinyl)-1H-1,2,3-triazol-4-yl]-3-pyridinyl](2-chlorophenyl)-methanone, and {2-[1-(3,5-bistrifluoromethylbenzyl)-5-pyridin-4-yl-1H-[1,2,3]triazol-4-yl]-pyridin-3-yl}-(2-chlorophenyl)-methanone, and is also known as VLY-6868, formerly LY686017. Crystalline Forms IV and V of tradipitant are disclosed in U.S. Pat. No. 7,381,826, and a process for preparing crystalline {2-[1-(3,5-bistrifluoromethylbenzyl)-5-pyridin-4-yl-1H-[1,2,3]triazol-4-yl]-pyridin-3-yl}-(2-chlorophenyl)-methanone, Form IV is disclosed in U.S. Pat. Nos. 8,772,496 and 9,708,291.

U.S. Pat. No. 7,320,994 describes methods for using compounds, such as tradipitant, for treating a condition associated with an excess of tachykinins, most particularly where the conditions associated with an excess of tachykinins are depression and anxiety. U.S. Pat. No. 7,320,994 further describes the use of compounds such as tradipitant in other such diseases, i.e., because these compounds inhibit the physiological effects associated with an excess of tachykinins. The patent describes the usefulness of such compounds in the treatment of numerous other disorders related to tachykinin receptor activation including psychosis, schizophrenia, and other psychotic disorders; neurodegenerative disorders such as dementia, including senile dementia of the Alzheimer's type, Alzheimer's disease, AIDS-associated dementia, and Down syndrome; demyelinating diseases such as multiple sclerosis and amyotrophic lateral sclerosis and other neuropathological disorders, such as peripheral neuropathy, diabetic and chemotherapy-induced neuropathy, and post-herpetic and other neuralgias; acute and chronic obstructive airway diseases such as adult respiratory distress syndrome, bronchopneumonia, bronchospasm, chronic bronchitis, drivercough, and asthma; inflammatory diseases such as inflammatory bowel disease, psoriasis, fibrositis, osteoarthritis, and rheumatoid arthritis; disorders of the musculoskeletal system, such as osteoporosis; allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczematoid dermatites; addiction disorders such as alcoholism; stress-related somatic disorders; reflex sympathetic dystrophy such as shoulder/hand syndrome; dysthyrnic disorders; adverse immunological reactions such as rejection of transplanted tissues and disorders related to immune enhancement or suppression such as systemic lupus erythematosis; gastrointestinal disorders or diseases associated with the neuronal control of viscera such as ulcerative colitis, Crohn's disease and irritable bowel syndrome; disorders of bladder function such as bladder detrusor hyperreflexia and incontinence; atherosclerosis; fibrosin and collagen diseases such as scleroderma and eosinophilic fascioliasis; irritative symptoms of benign prostatic hypertrophy; disorders associated with blood pressure, such as hypertension; or disorders of blood flow caused by vasodilation and vasospastic diseases, such as angina, migraine, and Reynaud's disease; emesis, including chemotherapy-induced nausea and emesis; and pain or nociception, for example, that attributable to or associated with any of the foregoing conditions. Finally, the patent describes such compounds are effective in amounts expected to vary from about 0.001 mg/kg/day to about 100 mg/kg/day.

Tradipitant is known to be therapeutically administered through a variety of routes of administration by which it is bioavailable. U.S. Pat. No. 7,320,994 discloses administration of tradipitant by oral and parenteral routes, e.g., orally, by inhalation, subcutaneously, intramuscularly, intravenously, transdermally, intranasally, rectally, occularly, topically, sublingually, and buccally, with oral administration being generally preferred for treatment. Additionally, use of tradipitant in the treatment of pruritus and atopic dermatitis is disclosed in international patent application publication WO 2016/141341, in gastric motility disorders including gastroparesis in international patent application publication WO 2019/099883, and in motion sickness in international patent application publication WO 2020/069092.

SUMMARY OF THE INVENTION

An aspect of the invention provides a method of treatment of a patient diagnosed with a lower respiratory tract infection, the method comprising: administering to the patient tradipitant at a dose effective to treat the lower respiratory tract infection or at least one symptom thereof. The lower respiratory tract infection may be a viral infection, and may further be viral pneumonia, which may be acute in presentation. The viral pneumonia may be caused or accompanied by infection with SARS-CoV2, i.e. COVID-19 infection, influenza infection, or other viral respiratory illness. According to some aspects, in addition to tradipitant treatment, the patient may be hospitalized and may be treated according to standard of care for the particular lower respiratory tract infection diagnosed, including use of invasive mechanical ventilation, extracorporeal membrane oxygenation (ECMO), non-invasive ventilation, a high flow oxygen device, or supplemental oxygen as indicated. Symptoms of the lower respiratory tract infection may include, e.g., fever, shortness of breath, cough, pneumonia, evidence of inflammatory lung injury, and other symptoms.

Treatment of the patient may include oral administration of a solid immediate release form comprising tradipitant and one or more pharmaceutically acceptable excipients, wherein the tradipitant dose is 100 to 400 mg/day, 100 to 300 mg/day, or 100 to 200 mg/day; 150 to 400 mg/day, 150 to 300 mg/day, or 150 to 200 mg/day; about 170 mg/day; or about 85 mg twice daily (bid). The tradipitant may alternatively be orally administered in a solid controlled release form comprising tradipitant and one or more pharmaceutically acceptable excipients, or orally or intravenously in a liquid suspension form. Treatment may continue for a course of 7 days, 14 days, or longer, e.g., in cases requiring hospitalization exceeding 14 days. Treatment may further include co-administration with an antiviral therapeutic such as, e.g., remdesivir.

In the context of aspects of the present invention, treatment of the lower respiratory tract infection is considered to include, but is not limited to: shortening a duration of time before the patient achieves clinical improvement, accelerating a recovery from the lower respiratory tract infection, preventing, slowing, or attenuating progression of the lower respiratory tract infection in the patient, complete resolution of symptoms, preventing respiratory deterioration in the patient, and/or preventing pulmonary injury to the patient following recovery from the lower respiratory tract infection.

A second aspect of the invention provides tradipitant for use in any of the preceding methods of treatment.

A third aspect of the invention provides a pharmaceutical composition comprising tradipitant for use in any of the preceding methods.

A fourth aspect of the invention provides tradipitant for use in the manufacture of a pharmaceutical composition comprising tradipitant for use in any of the preceding methods.

These and other aspects, advantages and salient features of the invention will become apparent from the following detailed description, which disclose embodiments of the invention.

Figure 1:
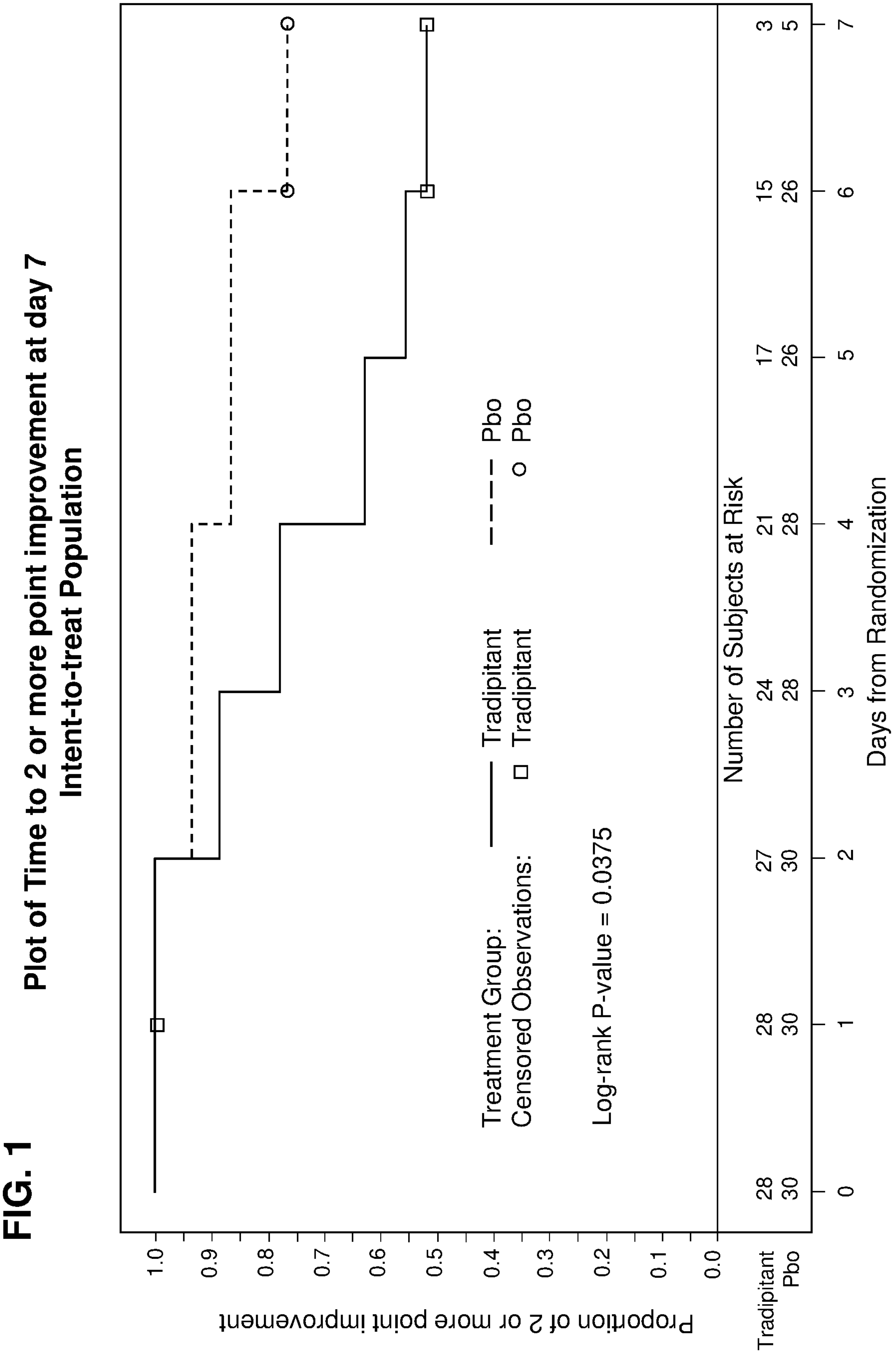
FIG. 1 illustrates a plot of time to 2 or more point improvement at day 7 in the intent-to-treat (ITT) population described in Example 1 herein.

The drawings are intended to depict only typical aspects of the disclosure, and therefore should not be considered as limiting the scope of the disclosure.

DETAILED DESCRIPTION

In various embodiments of the invention, the methods described herein include methods for the treatment of a patient diagnosed with a lower respiratory tract infection, i.e., an infectious disease causing lung injury. Causes of lower respiratory tract infections are known in the art. However, in various embodiments the lower respiratory tract infection is a viral disease or infection, or more particularly a viral respiratory infection. Such viral infections may include, e.g., coronavirus disease (COVID-19) and pneumonia associated therewith, and pneumonia caused by or associated with infection with other viruses, e.g., Severe Acute Respiratory Syndrome (SARS) coronavirus (SARS-CoV), influenza, and pneumonia secondary to a common cold such as those caused by rhinoviruses, coronaviruses, or respiratory syncytial virus (RSV). In other embodiments the lower respiratory tract infection may be bacterial pneumonia, including that caused by infection with, e.g., *Streptococcus pneumoniae*. The methods described herein may be applicable to the treatment of patients who have a confirmed diagnosis of infectious disease, or who are suffering from symptoms of suspected infectious disease, e.g., suspected infection with COVID-19, SARS, influenza, et al.

As used herein, treatment of the lower respiratory tract infection may be considered to include a reduction in severity of symptoms, the prevention or attenuation of progression, or the complete resolution of one or more symptoms of the lower respiratory tract infection, e.g. COVID-19, acute pneumonia, and other infections, after such symptom or symptoms have manifest in the patient. For example, a reduction in severity may include successful transition from invasive mechanical ventilation to non-invasive ventilation or high flow oxygen device, from these forms of respiratory support to mere supplemental oxygen, successful withdrawal of supplemental oxygen, and hospital discharge. Prevention or attenuation of progression may include, e.g., the avoidance of escalation from a requirement for supplemental oxygen to a requirement for more invasive ventilation and respiratory support. Treatment may particularly include the prevention or reduction of inflammatory lung injury caused by the infectious disease, including resolution of acute respiratory distress syndrome (ARDS).

Treatment is also considered to include the acceleration of achievement of clinical improvement. Such acceleration may shorten the time course of the illness and result in earlier recovery than would be achieved in the absence of such treatment. Such acceleration may also shorten the duration of time in which particular respiratory supports such as, e.g., mechanical ventilation, are required. Such treatment with tradipitant may include decreased total hospitalization time, decreased intensive care unit (ICU) time, decreased time during which a patient requires oxygen support including, e.g., cannula, high flow, ventilator, etc., and prevention of escalation resulting in hospitalization in patients whose illness is not severe enough to warrant hospitalization.

Treatment may further include the exertion of antiviral effects in vivo by interrupting either the entry of the virus, or the post-entry viral assembly, or by exposing the virus to other antiviral agents. Antiviral agents such as, e.g., remdesivir and others as known in the art may further be administered to the patient in combination with tradipitant.

In other embodiments, treatment may include improvement in long term pulmonary function or prevention of long term pulmonary functional deficits following recovery from viral pneumonia caused by infection with, e.g., COVID-19. Long term pulmonary functional deficits associated with, and remaining well after recovery from acute viral pneumonia are known in the art.

In some embodiments of the invention, treatment may or may not improve the clinical presentation of the patient during illness with the infectious disease, e.g., COVID-19. For example, treatment may reduce the time course or duration of the illness but may or may not reduce the severity of the illness prior to recovery. Regardless, such treatment may act to prevent long term lung damage caused by the viral pneumonia. Thus, treatment may include the use in prevention of post-viral pulmonary function deficits and pulmonary fibrosis.

In one aspect, a method of treatment of a patient diagnosed with an infectious disease capable of causing inflammatory lung injury, e.g. COVID-19, is provided which includes administering to the patient tradipitant. The tradipitant may be orally administered in a solid immediate release form comprising tradipitant and one or more pharmaceutically acceptable excipients. Alternatively, the tradipitant may be orally administered in a solid controlled release form comprising tradipitant and one or more pharmaceutically acceptable excipients. Solid controlled release forms may contain a relatively greater amount of tradipitant than solid immediate release forms, and may be administered at less frequent intervals, e.g., once per day (qd) rather than twice per day (bid). Still further, the tradipitant may be administered in liquid suspension form, either orally or intravenously. The tradipitant administered to the patient may be in crystalline Form IV or Form V regardless of dosage form or administration route.

Where solid immediate release forms are used, dosages of tradipitant may include, e.g., about 100-400 mg/day, about 150-400 mg/day, about 100-300 mg/day, about 150-300 mg/day, about 100-200 mg/day, about 170-340 mg/day, or about 170-255 mg/day. In certain embodiments, the amount may be about 170 mg/day of tradipitant. More particularly, the dosage may be 85 mg twice daily (bid), or 85 mg every 12 hours (Q12H). The foregoing dosages of tradipitant are known from, e.g., international patent application publications WO 2016/141341 and WO 2019/055225, which are incorporated herein by reference as though fully set forth, to be sufficient in amount and frequency to provide tradipitant exposures consistent with achievement and maintenance of tradipitant plasma concentration levels of at least about 100 ng/mL, at least about 125 ng/mL, at least about 150 ng/mL, at least about 175 ng/mL, at least about 200 ng/mL, or about 225 ng/mL or greater for the duration of the treatment regimen. The duration of the treatment regimen may be up to and including seven (7) days, fourteen (14) days or, if the patient is hospitalized, greater than such period, e.g., until discharge from the hospital.

Tradipitant administered as described herein may be effective to provide beneficial anti-inflammatory effects, to prevent, slow, or attenuate the progression of COVID-19 related inflammatory lung injury in the patient suffering from COVID-19, and/or to accelerate time to recovery from the infection.

In another embodiment, a method is provided for treating a patient suffering from pneumonia associated with or symptoms of suspected or confirmed infectious disease, e.g., COVID-19. Such symptoms may include, e.g., fever (defined as temperature ≥36.6° C. armpit, ≥37.2° C. oral, or ≥37.8° C. rectal), cough, pneumonia as confirmed by chest radiograph or CT scan, low oxygen saturation (defined as less than 92%), or evidence of inflammatory lung injury. Alternatively, the patient may have a confirmed laboratory diagnosis of COVID-19 infection by RT-PCR, and/or may be determined to meet severe or critical criteria of COVID-19 infection as defined by a treating hospital.

In this embodiment, the method comprises orally administering to the patient tradipitant, e.g., in crystalline Form IV or Form V. In some embodiments, the tradipitant may be orally administered in a solid immediate release form containing a tradipitant dose of about 100-400 mg/day, about 150-400 mg/day, about 100-300 mg/day, about 150-300 mg/day, about 100-200 mg/day, about 170-340 mg/day, or about 170-255 mg/day, about 170 mg/day of tradipitant, about 85 mg bid, or 85 mg Q12H. The duration of the treatment regimen may be up to and including seven (7)

days, fourteen (14) days, or, if the patient is hospitalized, greater than such period, e.g., until discharge from the hospital.

As described above, the tradipitant may be orally administered in a solid immediate release form comprising tradipitant and one or more pharmaceutically acceptable excipients, or alternatively, may be orally administered in a solid controlled release form comprising tradipitant and one or more pharmaceutically acceptable excipients. Still further, the tradipitant may be administered in liquid suspension form, either orally or intravenously. Regardless of the form or route of administration, such administration may have the effect of reducing inflammation, and preventing, slowing, or attenuating the progression of disease-related inflammatory lung injury, and may further include the exertion of antiviral effects in vivo by interrupting either the entry of the virus, or the post-entry viral assembly, or by exposing the virus to other antiviral agents.

In a further aspect of the invention, a method is provided for reducing inflammation, preventing inflammatory lung injury, or slowing or attenuating the progression of inflammatory lung injury in a patient suffering from an infectious disease which may be, e.g., COVID-19. In this embodiment, the method comprises orally administering to the patient tradipitant, e.g., in crystalline Form IV or Form V. In some embodiments, the tradipitant may be orally administered in a solid immediate release form containing a tradipitant dose of about 100-400 mg/day, about 150-400 mg/day, about 100-300 mg/day, about 150-300 mg/day, about 100-200 mg/day, about 170-340 mg/day, or about 170-255 mg/day, about 170 mg/day of tradipitant, about 85 mg bid, or 85 mg Q12H. The duration of the treatment regimen may be up to and including seven (7) days, fourteen (14) days or, if the patient is hospitalized, greater than such period, e.g., until discharge from the hospital.

As described above, the tradipitant may be orally administered in a solid immediate release form comprising tradipitant and one or more pharmaceutically acceptable excipients, or alternatively, may be orally administered in a solid controlled release form comprising tradipitant and one or more pharmaceutically acceptable excipients. Still further, the tradipitant may be administered in liquid suspension form, either orally or intravenously.

A further embodiment provides a method of treating a patient suffering from an infectious disease, e.g., COVID-19, and preventing deterioration of the patient's respiratory function. In such an embodiment, deterioration of respiratory function is defined as having an oxygen saturation of less than 92%. In this embodiment, the method comprises orally administering to the patient tradipitant, e.g., in crystalline Form IV or Form V. In some embodiments, the tradipitant may be orally administered in a solid immediate release form containing a tradipitant dose of about 100-400 mg/day, about 150-400 mg/day, about 100-300 mg/day, about 150-300 mg/day, about 100-200 mg/day, about 170-340 mg/day, or about 170-255 mg/day, about 170 mg/day of tradipitant, about 85 mg bid, or 85 mg Q12H. The duration of the treatment regimen may be up to and including seven (7) days, fourteen (14) days or, if the patient is hospitalized, greater than such period, e.g., until discharge from the hospital.

As described above, the tradipitant may be orally administered in a solid immediate release form comprising tradipitant and one or more pharmaceutically acceptable excipients, or alternatively, may be orally administered in a solid controlled release form comprising tradipitant and one or more pharmaceutically acceptable excipients. Still further, the tradipitant may be administered in liquid suspension form, either orally or intravenously.

In a further embodiment, a method is provided for preventing pulmonary injury following recovery from an infectious disease, e.g., COVID-19, by administering tradipitant to the patient. In such an embodiment, the pulmonary injury may manifest as decreased lung capacity, i.e., pulmonary deficits. These deficits may be reduced relative to, e.g., pre-illness pulmonary function or lung capacity. In particular, the pulmonary injury may be pulmonary fibrosis.

In this embodiment, the method comprises orally administering to the patient tradipitant, e.g., in crystalline Form IV or Form V. In some embodiments, the tradipitant may be orally administered in a solid immediate release form containing a tradipitant dose of about 100-400 mg/day, about 150-400 mg/day, about 100-300 mg/day, about 150-300 mg/day, about 100-200 mg/day, about 170-340 mg/day, or about 170-255 mg/day, about 170 mg/day of tradipitant, about 85 mg bid, or 85 mg Q12H. The duration of the treatment regimen may be up to and including seven (7) days, fourteen (14) days or, if the patient is hospitalized, greater than such period, e.g., until discharge from the hospital.

As described above, the tradipitant may be orally administered in a solid immediate release form comprising tradipitant and one or more pharmaceutically acceptable excipients, or alternatively, may be orally administered in a solid controlled release form comprising tradipitant and one or more pharmaceutically acceptable excipients. Still further, the tradipitant may be administered in liquid suspension form, either orally or intravenously.

A further embodiment provides tradipitant for use in any of the preceding methods of treatment, a pharmaceutical composition comprising tradipitant for use in any of the preceding methods, and tradipitant for use in the manufacture of a pharmaceutical comprising tradipitant for use in any of the preceding methods.

In any of the foregoing embodiments, the patient's manifestation of COVID-19 may include inflammatory lung injury, a diagnosis of pneumonia, and/or and may further include severe or critical COVID-19 infection, either in the presence or absence of inflammatory lung injury. The patient's manifestation of COVID-19 may further include symptoms of fever and/or cough. Still further, the patient may have a diagnosis of COVID-19, which may be confirmed by diagnostic test or may be suspected, e.g. based on one or more of symptoms, medical history, and travel and/or exposure history.

The skilled artisan will appreciate that additional embodiments may be selected by combining the embodiments above, or by reference to the examples given herein.

Example 1

A randomized, double-blind, placebo-controlled study investigates the efficacy of tradipitant in the treatment of inflammatory lung injury and pneumonia associated with severe or critical COVID-19 infection, and improvement of clinical outcomes associated with severe or critical COVID-19 infection. Such improvements in clinical outcomes include reduction in long term pulmonary function deficits and pulmonary fibrosis.

Methods: Prospective participants attend a screening visit on study day −1 to 0 to assess the prospective patient's eligibility to participate. All enrolled patients are asked to undertake an initial physical examination and must satisfy inclusion and exclusion criteria before being enrolled into the study. A total sample size of 300 patients (150 per arm) provides approximately 93% power to detect a 20% difference of normalization in fever and oxygen saturation, assuming 50% and 70% normalization rates in placebo and tradipitant treatment groups respectively, based on a two-sided Fisher's Exact Test at a 5% significance level.

Inclusion criteria include: adults aged 18-90; confirmed laboratory COVID-19 infection by RT-PCR; confirmed pneumonia by chest radiograph or computed tomography; fever defined as temperature ≥36.6° C. armpit, ≥37.2° C. oral, or ≥37.8° C. rectal; and oxygen saturation of less than 92% on room air OR on mechanical ventilation OR increased work of breathing (WOB) on exam without respiratory support OR respiratory rate greater than 20 per minute. Exclusion criteria include: recent use of illicit drugs or alcohol abuse; known allergy to tradipitant or other neurokinin-1 antagonists; pregnancy; known HIV, HBV, or HCV infection; malignant tumor, other serious systemic diseases; and inability to provide informed consent or to have an authorized relative or designated person provide informed consent, or to comply with the protocol requirements.

Patients who meet the inclusion-exclusion criteria are randomized 1:1 to treatment with either 85 mg tradipitant twice daily (bid) per os (PO, i.e. orally) or matching placebo under double-blind conditions, in addition to standard of care for COVID-19 infection according to protocol at the treating hospital. In both arms, treatment with study medication continues for 14 days or until discharge from the hospital. In both tradipitant treatment and placebo study arms, patients are given one capsule of study medication to be taken orally every day in the morning prior to or at 9:00 am and one capsule of study medication to be taken orally every day in the evening approximately 12 hours later (±1 hour). Patients in the tradipitant treatment arm receive capsules containing 85 mg tradipitant, as well as spray-dried lactose monohydrate, microcrystalline cellulose (Avicel PH102 and PH200), povidone, croscarmellose sodium, sodium lauryl sulfate, and magnesium stearate as excipients. The tradipitant capsules are white opaque, hard gelatin capsules. Placebo capsules are provided in size and appearance identical to those containing tradipitant.

For patients requiring administration via nasogastric tube, the following procedure is used: 1) empty contents of one 85 mg capsule in a glass mortar and grind using a pestle until all granules are thoroughly crushed; 2) add 10 mL of water while continuing to grind to obtain a uniform dispersion; 3) draw up entire dispersion into a suitable syringe; 4) connect syringe tip to nasogastric tube and push entire syringe contents; and 5) rinse mortar and pestle with 5 mL of water and repeat steps 3) and 4). The crushing procedure results in the preparation of a uniform dispersion in water, which can then be administered through a nasogastric tube without clogging.

Patient assessments are performed in accordance with the schedule of evaluations detailed in Table 1 below.

TABLE 1

Schedule of Evaluations

| Period | Pre-randomization Screening | Evaluation Assessment | EOS/ET |
|---|---|---|---|
| Visit | 1 | 2 | 3 |
| Informed Consent Form[1] | X | | |
| Inclusion/Exclusion Criteria | X | | |
| Demographics | X | | |
| Participant ID Assignment | X | | |
| Randomization | | Day 1 | |
| Medical History | X | | |
| Hematology[2] | X | | X |
| Markers of Infection and Inflammation | X | Daily | X |
| Oxygen Saturation | X | Daily | X |
| NEWS2 | X | Daily | X |
| NRS cough[5] | X | Daily | X |
| Chemistry[2] | X | | X |
| Urinalysis[2] | X | | X |
| Drug/Alcohol Screen | X | | |
| Serum B-HCG (WOCBP) | X | | |
| PG Blood Sample | X | | |
| Vital Signs[3] | X | Daily | X |
| Physical Examination | X | | X |
| ECG[4] | X | | X |
| Chest X ray or CT chest | X | | |
| Clinical status 7 point ordinal scale | X | Daily | X |
| Drug Administration | | Daily | |
| EOS | | | X |
| Adverse Events Query | X | Daily | X |
| Prior/Concomitant Medications | X | Daily | X |

EOS = end of study; ET = early termination; WOCBP = women of childbearing potential; PG = Pharmacogenetic; NEWS2 = National Early Warning Score 2; CT = Computed tomography

[1] The Study Informed Consent will be explained to the subjects at the screening visit and must be signed prior to performing any procedures.

[2] Laboratory tests will be repeated as required to follow any abnormal changes.

[3] Body height will be recorded at screening only. Weight will only be collected at Sreening and EOS/ET.

[4] An auto-interpretation from the provided ECG machines will be used to determine any cardiac abnormalities

[5] To be performed only if possible, subject is not intubated.

Oxygen saturation is measured daily using a pulse oximeter as specified in Table 1. A pulse oximeter measures the blood oxygen level (SpO2). Criteria for oxygen normalization are peripheral capillary oxygen saturation (Sp02) >94% sustained for at least 24 hours.

Body temperature is measured daily, as specified in Table 1. Criteria for fever normalization include a temperature that is lower than 36.6° C. armpit, lower than 37.2° C. oral, or lower than 37.8° C. rectal, sustained for at least 24 hours.

Nasopharyngeal swabs are collected to detect the viral load of COVID-19 by polymerase chain reaction (PCR). This daily assessment is part of the markers of infection and inflammation and is performed as indicated in the Schedule of Evaluations (Table 1).

NEWS is a tool developed by the Royal College of Physicians and subsequently updated to NEWS2 in 2017. The NEWS2 score identifies acute deterioration, including sepsis of hospitalized patients. It is based on a simple aggregate scoring system of six physiological parameters: respiration rate, oxygen saturation, systolic blood pressure, pulse rate, level of consciousness or new confusion, and temperature. NEWS2 is assessed at the intervals indicated in Table 1.

Mortality is assessed as the proportion of participants with in-hospital mortality, and is evaluated per treatment arm.

The severity of cough is assessed using the numerical rating scale (NRS) for cough. For this scale, the physician or designee rates the participant's cough from 0 (no cough at all) to 10 (maximal cough). Assessment is performed as indicated in the Schedule of Evaluations (Table 1).

Clinical status is assessed daily during hospitalization using a 7 point ordinal scale, with scores defined as follows: 1) Death; 2) Hospitalized, on invasive mechanical ventilation or extracorporeal membrane oxygenation (ECMO); 3) Hospitalized, on non-invasive ventilation or high flow oxygen devices; 4) Hospitalized, requiring supplemental oxygen; 5) Hospitalized, not requiring supplemental oxygen; 6) Not hospitalized, limitation on activities; and 7) Not hospitalized.

Markers of infection and inflammation are collected daily (Table 1) and are used to quantify and assess reduction in inflammation and inflammatory lung injury, including: ferritin; CRP; CBC with differential; IL-1 beta, IL-2, IL-4, IL-6, IL-7, IL-10, IL-37; granulocyte-colony stimulating factor; interferon-gamma; viral load of COVID-19; PT/PTT/INR; D-Dimer, BNP, ESR; Troponin-1 and T; TNF-alpha; and Inducible protein 10.

Efficacy of tradipitant in the treatment of COVID-19 is assessed according to the following measures: improvement, and time to improvement in clinical status as assessed by 7-point ordinal scale as compared to baseline; proportion of participants with normalization of fever and oxygen saturation at day 14; change from baseline of inflammatory lung markers, including interleukin-6 (IL-6), collected once per day in the morning; rate of decline of viral load of COVID-19, assessed by RT-PCR from nasopharyngeal samples; proportion of participants with in-hospital mortality; mean change in NEWS2 score from baseline, assessed at screening and daily following randomization; and reduction of cough from baseline as measured by NRS (numerical rating scale) for cough, assessed at screening and daily in the morning following randomization, if possible.

Results: An interim analysis of the first sixty enrolled patients assesses the safety and efficacy of tradipitant in this population of COVID-19 patients. The demographics of this Intention-to-Treat population are provided in Table 2.

TABLE 2

Baseline Demographic Summary. Intention-to-Treat Population

| Characteristic Statistic | Tradipitant (N = 28) | Placebo (N = 30) | Total (N = 58) |
|---|---|---|---|
| Age (years) | 71.0 (62.5-77.5) | 66.5 (58.0-72.0) | 68.5 (61.0-77.0) |
| Sex, n (%) | | | |
| Male | 20 (71.4) | 20 (66.7) | 40 ( 69.0) |
| Female | 8 (28.6) | 10 (33.3) | 18 (31.0) |
| Any Comorbidities, n (%) | 27 (96.4) | 28 (93.3) | 55 (94.8) |
| Hypertension | 11 (39.3) | 15 (50.0) | 26 (44.8) |
| Diabetes | 8 (28.6) | 7 (23.3) | 15 (25.9) |
| Coronary Heart Disease | 1 (3.6) | 4 (13.3) | 5 (8.6) |
| Asthma | 1 (3.6) | 4 (13.3) | 5 (8.6) |
| 7 Point Ordinal Scale at Baseline, n (%) | | | |
| 2 - Hospitalized on mechanical ventilation or ECMO | 4 ( 14.3) | 2 ( 6.7) | 6 (10.3) |
| 3 - Hospitalized on non-invasive ventilation or high-flow oxygen supplement | 13 ( 46.4) | 12 (40.0) | 25 (43.1) |
| 4 - Hospitalized requiring supplemental oxygen | 9 (32.1) | 16 (53.3) | 25 (43.1) |
| 5 - Hospitalized not requiring supplemental oxygen, requiring continued medical care | 2 ( 7.1) | 0 ( 0.0) | 2 ( 3.4) |
| Time from Hospitalization to Starting Study Treatment, Days | 4.0 (2.0-6.5) | 6.0 (2.0-12.0) | 4.0 (2.0-9.0) |
| Early (<=10 Days from Hospitalization) | 23 (82.1) | 22 (73.3) | 45 (77.6) |
| Late (>10 Days from Hospitalization) | 5 ( 17.9) | 8 (26.7) | 13 (22.4) |
| Highest Oxygen Therapy Support, n (%) | | | |
| Room Air | 1 ( 3.6) | 0 ( 0.0) | 1 ( 1-7) |
| Nasal Cannula (NC) | 5 ( 17.9) | 6 (20.0) | 11 ( 19.0) |
| Non Rebreather (NRB) | 1 ( 3.6) | 2 ( 6.7) | 3 (5.2) |
| High Flow Nasal Cannula (HFNC) | 6 (21.4) | 9 (30.0) | 15 (25.9) |
| CPAP Mask | 0 ( 0.0) | 2 ( 6.7) | 2 ( 3.4) |
| BiPAP Mask | 1 ( 3.6) | 1 ( 3.3) | 2 ( 3.4) |
| Mechanical Ventilation | 14 (50.0) | 10 (33.3) | 24 (41.4) |

% = 100 x n/N. Data are median (IQR).

Clinical status is assessed on the 7 point ordinal scale described above. Clinical improvement is defined as at least a 2 point improvement in the 7 point ordinal scale. 57% of patients in the tradipitant arm show clinical improvement, while 50% of patients in the placebo arm show clinical improvement. The tradipitant arm has a mortality rate of 14.2%, while the placebo arm has a mortality rate of 16.6%. In each of these measures, patients in the tradipitant arm show superior outcomes, although not by a statistically significant margin.

In the time to improvement analysis, patients treated with tradipitant recover earlier than those receiving placebo (FIG. 1). As shown in table 3, this difference is statistically significant (HR=2.55, p=0.0375) at day 7 of treatment, and is generally consistent among patients of varying degree of severity at baseline. Table 3 provides 7-day overall outcomes and outcomes according to baseline ordinal scale score (baseline ordinal scale scores of 4, 3, and 2).

TABLE 3

Outcomes Overall and According to Score on the Ordinal Scale at Day 7, Intention-to-Treat Population

| | Overall* | | Ordinal Score at Baseline* 4 | | 3 | | 2 | |
|---|---|---|---|---|---|---|---|---|
| | Tradipitant (N = 28) | Placebo (N = 30) | Tradipitant (N = 9) | Placebo (N = 16) | Tradipitant (N = 13) | Placebo (N = 12) | Tradipitant (N = 4) | Placebo (N = 2) |
| **Responder as Improvement of 2 or More Points** | | | | | | | | |
| No. of responders | 13 | 7 | 6 | 6 | 2 | 1 | 3 | 0 |
| Median time to responder (95% CI) - days | • (4-NE) | • (NE-NE) | 4(3-NE) | • (4-NE) | • (5-NE) | • (NE-NE) | 4 (2-NE) | • (NE-NE) |
| Hazard ratio (95% CI)** | 2.55 (1.02-6.42 [0.0461]) | | 2.23 (0.71-6.98 [0.1673]) | | 2.19 (0.20-24.18 [0.5225]) | | NE (0.00-NE [0.9983]) | |
| Mortality | | | | | | | | |
| Hazard ratio (95% CI)† | 2.65 (0.24-29.29 [0.4255]) | | 3.14 (0.20-50.23 [0.4186]) | | . (NE - NE [NE]) | | NE (0.00-NE [0.9985]) | |
| No. of deaths by day 7 | 2 | 1 | 1 | 1 | 0 | 0 | 1 | 0 |
| KM estimate - % | 9.8 | 3.8 | 25.0 | 8.3 | 0.0 | 0.0 | 25.0 | 0.0 |
| (95% CI) | (2.5-33.8) | (0.6-24.3) | (3.9-87.2) | (1.2-46.1) | (0.0-0.0) | (0.0-0.0) | (3.9-87.2) | (0.0-0.0) |
| **Ordinal Score at Day 7 Days - no. (%)‡** | | | | | | | | |
| Patients with baseline and day 7 score data | 28 | 30 | 9 | 16 | 13 | 12 | 4 | 2 |
| 1 | 2 (7.1) | 1 (3.3) | 1 (11-1) | 1 (6.3) | 0 (0.0) | 0 (0.0) | 1 (25.0) | 0 (0.0) |
| 2 | 9 (32.1) | 8 (26.7) | 0 (0.0) | 2 (12.5) | 8 (61.5) | 4 (33.3) | 1 (25.0) | 2 (100.0) |
| 3 | 4 (14.3) | 5 (16.7) | 1 (11-1) | 1 (6.3) | 3 (23.1) | 4 (33.3) | 0 (0.0) | 0 (0.0) |
| 4 | 2 (7.1) | 9 (30.0) | 1 (11-1) | 6 (37.5) | 0 (0.0) | 3 (25.0) | 1 (25.0) | 0 (0.0) |
| 5 | 2 (7.1) | 0 (0.0) | 0 (0.0) | 0 (0.0) | 1 (7.7) | 0 (0.0) | 1 (25.0) | 0 (0.0) |
| 7 | 9 (32.1) | 7 (23.3) | 6 (66.7) | 6 (37.5) | 1 (7.7) | 1 (8.3) | 0 (0.0) | 0 (0.0) |
| Odds ratio (95% CI) | 1.05 (0.42-2.63 [0.9149]) | | 0.40 (0.08-2.02 [0.2692]) | | 2.69 (0.60-12.18 [0.1980]) | | 0.43 (0.02-11.53 [0.6180]) | |

*P values and confidence intervals have not been adjusted for multiple comparisons. NE denotes not possible to estimate.
**Hazard ratios was calculated from the Cox model; P values for hazard ratios were calculated with the log-rank test. Hazard ratios bigger than I indicate a benefit for tradipitant.
†Hazard ratios was calculated from the Cox model; P values for hazard ratios were calculated with the log-rank test. Hazard ratios less than 1 indicate a benefit for tradipitant.
‡Odds ratios and P values were calculated with the use of a proportional odds model. Odds ratio values greater than I indicate a benefit for tradipitant.

Figure 2:
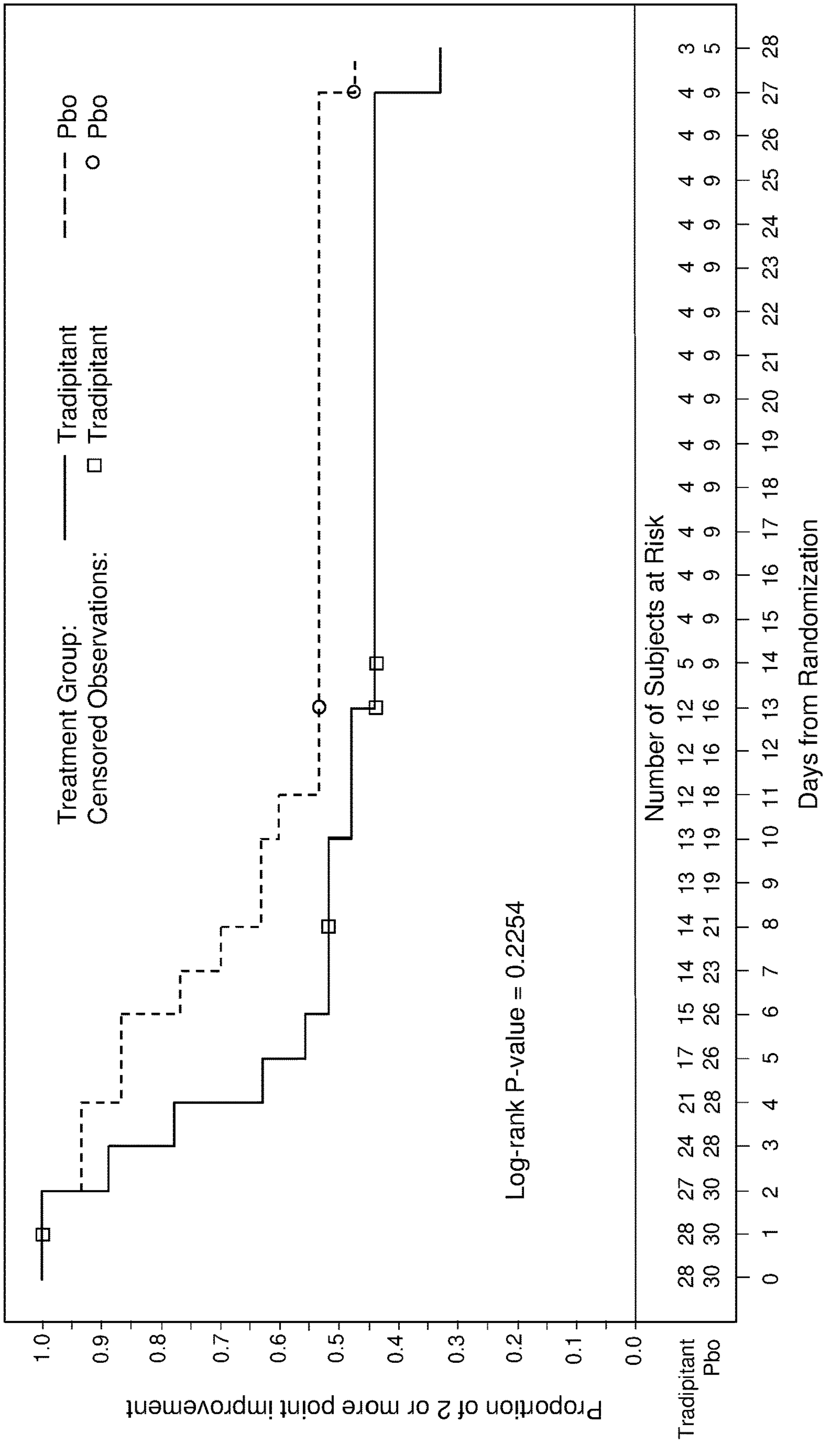
FIG. 2 illustrates a plot of time to 2 or more point improvement at day 28 in the intent-to-treat (ITT) population described in Example 1 herein.

Table 4 and FIG. 2 show that at day 28, tradipitant shows a numerical benefit over placebo, with an earlier median time to recovery (HR=1.55, p=0.2254, median time to improvement 10 days for tradipitant and 28 days for placebo). This benefit is generally consistent among patients of varying degree of severity at baseline. Table 4 provides 28-day overall outcomes and outcomes according to baseline ordinal scale score (baseline ordinal scale scores of 4, 3, and 2).

TABLE 4

Outcomes Overall and According to Score on the Ordinal Scale at Day 28. Intention-to-Treat Population

| | Overall* | | Ordinal Score at Baseline* 4 | | 3 | | 2 | |
|---|---|---|---|---|---|---|---|---|
| | Tradipitant (N = 28) | Placebo (N = 30) | Tradipitant (N = 9) | Placebo (N = 16) | Tradipitant (N = 13) | Placebo (N = 12) | Tradipitant (N = 4) | Placebo (N = 2) |
| **Responder as Improvement of 2 or More Points** | | | | | | | | |
| No. of responders | 16 | 15 | 7 | 11 | 4 | 4 | 3 | 0 |

TABLE 4-continued

Outcomes Overall and According to Score on the Ordinal Scale at Day 28. Intention-to-Treat Population

| | Overall* | | Ordinal Score at Baseline* 4 | | 3 | | 2 | |
|---|---|---|---|---|---|---|---|---|
| | Tradipitant (N = 28) | Placebo (N = 30) | Tradipitant (N = 9) | Placebo (N = 16) | Tradipitant (N = 13) | Placebo (N = 12) | Tradipitant (N = 4) | Placebo (N = 2) |
| Median time to responder (95% CI) - days | 10 (4-NE) | 27 (8-NE) | 4 (3-NE) | 9 (4-NE) | 27 (5-NE) | • (7-NE) | 4 (2-NE) | • (NE-NE) |
| Hazard ratio (95% CI)** | 1.55 (0.76-3.14 [0.2267]) | | 1.59 (0.61-4.15 [0.3396]) | | 1.08 (0.27-4.35 [0.9086]) | | NE (0.00-[0.9983]) | |
| Mortality | | | | | | | | |
| Hazard ratio (95% CI)† | 1.03 (0.28-3.85 [0.9610]) | | 1.24 (0.13-11.99 [0.8543]) | | 0.95 (0.06-15.26 [0.9731]) | | 1.84 (0.15-22.52 [0.6328]) | |
| No. of deaths by day 28 | 4 | 5 | 1 | 3 | 1 | 1 | 2 | 1 |
| KM estimate - % | 20.4 | 25.9 | 25.0 | 35.8 | 9.1 | 11.1 | 50.0 | 50.0 |
| (95% CI) | (8.2-45.7) | (11.5-52.2) | (3.9-87.2) | (12.4-77.5) | (1.3-49.2) | (1.6-56.7) | (15.5-94.2) | (9.0-99.4) |
| Ordinal Score at Day 28 Days - no. (%)‡ | | | | | | | | |
| Patients with baseline and day 28 score data | 28 | 30 | 9 | 16 | 13 | 12 | 4 | 2 |
| 1 | 4 (14.3) | 5 (16.7) | 1 (11-1) | 3 (18.8) | 1 (7.7) | 1 (8.3) | 2 (50.0) | 1 (50.0) |
| 2 | 8 (28.6) | 5 (16.7) | 0 (0.0) | 1 (6.3) | 8 (61.5) | 3 (25.0) | 0 (0.0) | 1 (50.0) |
| 3 | 1 (3.6) | 2 (6.7) | 1 (11-1) | 0 (0.0) | 0 (0.0) | 2 (16.7) | 0 (0.0) | 0 (0.0) |
| 4 | 0 (0.0) | 3 (10.0) | 0 (0.0) | 1 (6.3) | 0 (0.0) | 2 (16.7) | 0 (0.0) | 0 (0.0) |
| 7 | 15 (53.6) | 15 (50.0) | 7 (77.8) | 11 (68.8) | 4 (30.8) | 4 (33.3) | 2 (50.0) | 0 (0.0) |
| Odds ratio (95% CI) | 1.01 (0.38-2.67 [0.9795]) | | 0.62 (0.09-4.02 [0.6119]) | | 2.21 (0.50-9.71 [0.2941]) | | 0.43 (0.02-12.22 [0.6242]) | |

*P values and confidence intervals have not been adjusted for multiple comparisons. NE denotes not possible to estimate.

**Hazard ratios was calculated from the Cox model; P values for hazard ratios were calculated with the log-rank test. Hazard ratios bigger than I indicate a benefit for tradipitant.

†Hazard ratios was calculated from the Cox model; P values for hazard ratios were calculated with the log-rank test. Hazard ratios less than 1 indicate a benefit for tradipitant.

‡Odds ratios and P values were calculated with the use of a proportional odds model. Odds ratio values greater than I indicate a benefit for tradipitant.

These data indicate that tradipidant accelerates time to clinical improvement in patients with severe or critical COVID-19 infection, and that hospitalized patients with COVID-19 pneumonia improve sooner when treated with tradipitant as compared to placebo. Given the relatively low mortality rate associated with COVID-19, a significantly larger study population is required in order to assess treatment effect on mortality rate.

The foregoing description of various aspects of the invention has been presented for purposes of illustration and description. It is not intended to be exhaustive or to limit the invention to the precise form disclosed, and modifications and variations are possible. Such modifications and variations that may be apparent to a person skilled in the art are intended to be included within the scope of the invention as defined by the accompanying claims.

We claim:

1. A method of treatment of a patient diagnosed with a lower respiratory tract infection, the method comprising:

administering to the patient tradipitant at a dose effective to treat the lower respiratory tract infection or at least one symptom thereof.

2. The method of claim 1, wherein the lower respiratory tract infection is a viral infection.

3. The method of claim 2, wherein the lower respiratory tract infection is viral pneumonia.

4. The method of claim 3, wherein the viral pneumonia is acute, and is caused or accompanied by one or more of: COVID-19 infection, influenza infection, SARS-CoV infection, rhinovirus infection, infection with a coronavirus other than SARS-CoV or SARS-CoV2, or respiratory syncytial virus (RSV) infection.

5. The method of claim 1, wherein the lower respiratory tract infection is a bacterial infection.

6. The method of claim 5, wherein the bacterial infection is caused by *Streptococcus pneumoniae.*

7. The method of claim 1, wherein the patient is hospitalized, and wherein the patient's treatment further includes one or more of: invasive mechanical ventilation, extracorporeal membrane oxygenation (ECMO), non-invasive ventilation, a high flow oxygen device, or supplemental oxygen.

8. The method of claim 1, wherein the at least one symptom of the lower respiratory tract infection is selected from the group consisting of: fever, shortness of breath, cough, pneumonia, oxygen saturation of less than 92%, and evidence of inflammatory lung injury.

9. The method of claim 1, wherein the treatment of the lower respiratory tract infection includes a shortening of a duration of time before the patient achieves clinical improvement.

10. The method of claim 1, wherein the treatment of the lower respiratory tract infection includes accelerating a recovery from the lower respiratory tract infection.

11. The method of claim 1, wherein the treatment of the lower respiratory tract infection includes preventing, slowing, or attenuating progression of the lower respiratory tract infection in the patient.

12. The method of claim 1, wherein the treatment of the lower respiratory tract infection includes preventing respiratory deterioration in the patient.

13. The method of claim 1, wherein the treatment of the lower respiratory tract infection includes preventing pulmonary injury following recovery from the lower respiratory tract infection.

14. The method of claim 1, wherein the treatment of the lower respiratory tract infection includes resolution of the lower respiratory tract infection or of one or more symptom thereof.

15. The method of claim 1, wherein the tradipitant is orally administered to the patient in a solid immediate release form comprising tradipitant and one or more pharmaceutically acceptable excipients, wherein the tradipitant dose is 150 to 400 mg/day, and wherein the tradipitant is in crystalline Form IV or Form V.

16. The method of claim 15, wherein the tradipitant dose is 170 mg/day, and wherein the dose of 170 mg/day is given as 85 mg twice daily (bid).

17. The method of claim 1, wherein the tradipitant is orally administered in a solid controlled release form comprising tradipitant and one or more pharmaceutically acceptable excipients.

18. The method of claim 1, wherein the tradipitant is orally or intravenously administered in a liquid suspension form.

19. The method of claim 1, wherein the tradipitant is administered to the patient for a course of seven (7) days or fourteen (14) days.

20. The method of claim 1, further comprising: administering the tradipitant to the patient in combination with an antiviral medication.

* * * * *